United States Patent

[19]

Huber

[11] Patent Number: 5,874,576

[45] Date of Patent: Feb. 23, 1999

[54] LIGHT SCREENING AGENTS

[75] Inventor: Ulrich Huber, Erlenbach, Switzerland

[73] Assignee: Givaudan-Roure (International) SA, Vernier-Geneve, Switzerland

[21] Appl. No.: 766,540

[22] Filed: Dec. 11, 1996

[30] Foreign Application Priority Data

Dec. 19, 1995 [CH] Switzerland .............................. 3580/95
Sep. 20, 1996 [CH] Switzerland .............................. 2305/96

[51] Int. Cl.$^6$ .................................................. C07D 251/42
[52] U.S. Cl. ........................................... 544/211; 544/194
[58] Field of Search ...................................... 544/194, 211

[56] References Cited

U.S. PATENT DOCUMENTS 3,896,125  7/1975  Helmo ...................................... 544/211

FOREIGN PATENT DOCUMENTS 0 709 080 A1  5/1996  European Pat. Off. .
1241452       1/1964  Germany .

*Primary Examiner*—Yogendra N. Gupta
*Attorney, Agent, or Firm*—George W. Johnston; Alan P. Kass; Mark E. Waddell

[57] ABSTRACT

A light screening agent, which contains a compound of the general formula

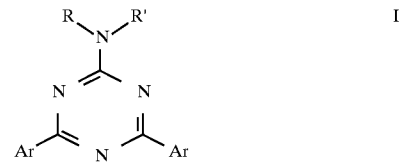

wherein R and R' are alkyl, hydroxyalkyl, alkenyl, alkynyl, or alkyl ether radicals substituted by one or more hydroxy and/or alkoxy groups and Ar represents one of the residues

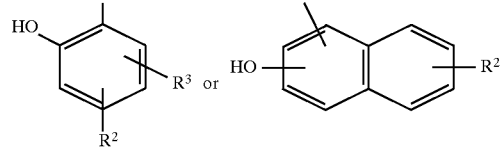

in which $R^2$ is hydroxy, alkyl, alkenyl, alkynyl, or an alkyl, alkenyl, alkynyl ether residue or polyalkyl ether residue optionally substituted by one or more hydroxy and/or alkoxy groups and $R^3$ is hydrogen or signifies a residue $R^2$ and in which the hydroxy group is present in the α-position to the bonding to the triazine nucleus, with the number of C and O atoms present in R and R' being a total of 8 to 42, especially 8 to 18, and the number of O atoms corresponding to at most half of the C atoms.

6 Claims, No Drawings

LIGHT SCREENING AGENTS

The invention relates to light screening agents and compositions, methods of using them and processes for their manufacture.

SUMMARY OF THE INVENTION

The light screening agent contains a compound of the general formula

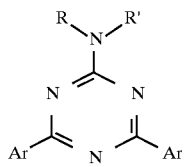
I wherein R and R' are alkyl, hydroxyalkyl, alkenyl, alkynyl, or alkyl ether radicals substituted by one or more hydroxy and/or alkoxy groups and Ar represents one of the residues

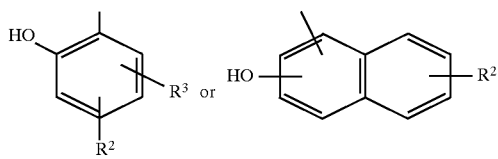

in which $R^2$ is hydroxy, alkyl, alkenyl, alkynyl, or an alkyl, alkenyl, alkynyl ether residue or polyalkyl ether residue optionally substituted by one or more hydroxy and/or alkoxy groups and $R^3$ is hydrogen or signifies a residue $R^2$ and in which the hydroxy group is present in the α-position to the bonding to the triazine nucleus, with the number of C and O atoms present in R and R' being a total of 8 to 42, especially 8 to 18, and the number of O atoms corresponding to at most half of the C atoms.

DETAILED DESCRIPTION

It is known that sunlight accelerates the ageing of skin and even gives rise to skin cancer, these undesired effects being caused primarily by the UV A radiation which directly tans the skin and which has wavelengths in the region of about 320 to 400 nm.

It has now been found that the compounds of the formula

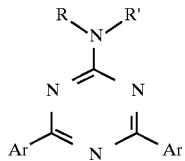
I wherein R and R' are alkyl, hydroxyalkyl, alkenyl, alkynyl, or alkyl ether radicals substituted by one or more hydroxy and/or alkoxy groups and Ar represents one of the residues

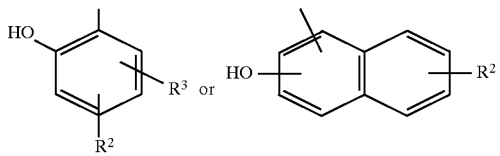

in which $R^2$ is hydroxy, alkyl, alkenyl, alkynyl, or an alkyl, alkenyl, alkynyl ether residue or polyalkyl ether residue optionally substituted by one or more hydroxy and/or alkoxy groups and $R^3$ is hydrogen or signifies a residue $R^2$ and in which the hydroxy group is present in the α-position to the bonding to the triazine nucleus, with the number of C and O atoms present in R and R' being a total of 8 to 42, especially 8 to 18, and the number of O atoms corresponding to at most half of the C atoms, are excellent UV A filters in that with outstanding skin compatibility and stability (light, heat, moisture) they bring about a strong reduction in the stress effect on the skin and therewith a delay in skin ageing. In particular, however, these UV A filters also have an outstanding photostability.

$C_1$–$C_{20}$-Alkyls such as methyl, ethyl, propyl, isopropyl, n-butyl, sec.butyl, isobutyl, pentyl, isopentyl, n-hexyl, n-octyl, 2-ethyl-hexyl, iso-nonyl, n-docecyl, hexadecyl, cocoyl, eicosyl and 3,7,11-trimethyl-dodecyl are examples of alkyl residues, C2–C12-alkenyls such as allyl, propenyl, methylpropenyl, ω-undecenyl, 2,4-dodecadienyl and 3,7-dimethyl-2,6-heptadienyl are examples of alkenyl residues, $C_2$–$C_{12}$-alkynyls such as ethynyl, propargyl, 2-methyl-4-pentynyl, ω-undecynyl and 3-dodecynyl are examples of alkynyl residues, $C_2$–$C_{20}$-alkyl ether residues such as 2-ethoxy-ethyl, 2-methoxy-1-methyl-ethoxy, 3-methyloxy-propyl, 3-(2-ethyl-hexyl)-oxy-propyl, 2-ethoxybutyl, methoxymethyl and 2-ethoxy-octadecanyl are examples of alkyl ether residues, allyl and propargyl are examples of alkenyl ether residues and alkynyl ether residues, respectively, $C_4$–$C_{20}$ residues such as 2-[2-(2-methoxy)-ethoxy]-ethyl, 2-[2-(2-hydroxy)ethoxy]-ethyl, 2-(2-ethoxy-1-methyl-ethoxy)-1-methyl-ethyl, 2-(2-{2-[2-(2-hydroxy-propoxy)-propoxy]-propoxy}-propoxy)-propyl, 2-(2-{2-[2-(2-(2-ethoxy-propoxy)-propoxy)-propoxy]-propoxy}-propoxy)-propyl and 2-(2-{2-[2-(2-(2-hydroxy-ethoxy)-ethoxy)-ethoxy]-ethoxy}-ethoxy)-ethyl are examples of polyoxalkyl ether residues, C4–C12-hydroxyalkyl ether residues such as 3-methoxy-2-hydroxy-propyl, 3-octyloxy-2-hydroxy-propyl and 3-iso-nonyloxy-2-hydroxy-propyl are examples of hydroxyalkyl ether residues, and $C_2$–$C_12$-alkyl alcohol residues such as 2-hydroxyethyl, 2-hydroxy-propyl and 2-hydroxy-1-methyl-ethyl, 2,3-dihydroxy-propyl and 2-hydroxy-dodecyl are examples of alkyl alcohol residues.

Examples of Ar residues are:

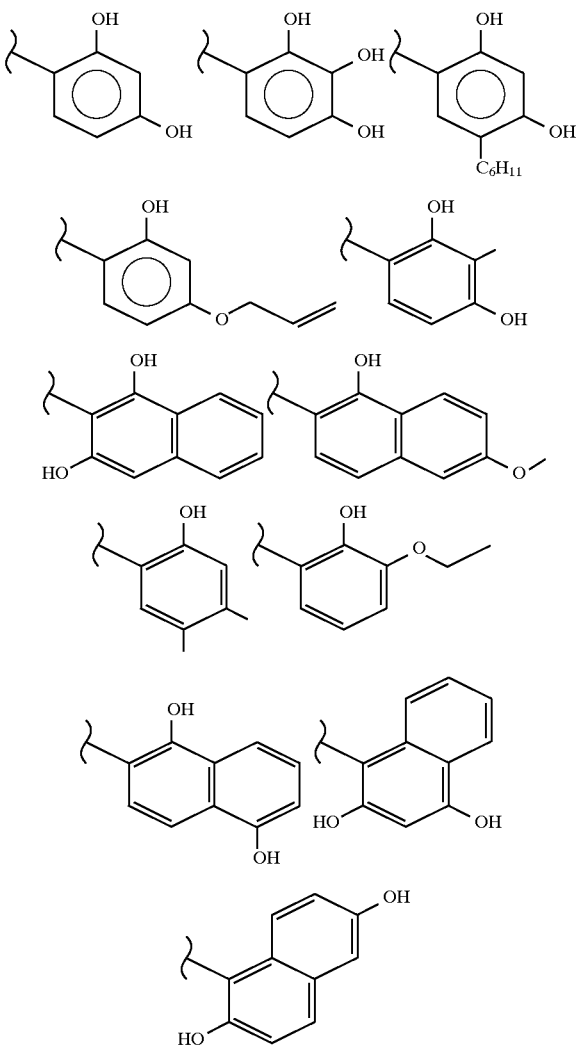

It has also been found that the compounds of formula I surprisingly increase the protective effect of UV B filters, i.e. of substances which absorb the erythema-producing UV-B radiation in the region of about 290 to about 320 nm, although the absorption maximum of the compound I does not lie in this region, but in the region of about 320 to 360 nm.

Objects of the invention are accordingly the novel compounds I their manufacture, light screening agents, namely light screening preparations for cosmetic purposes containing compounds of formula I above, preferably in combination with a UV B filter, and the use of compounds I as light screening agents, especially for cosmetic purposes.

In the latter case there are obtained light screening preparations which absorb the UV radiation in the entire region of 280 to 380 nm—a so-called "A+B total block"—and protect the skin from too early ageing and in many cases from light dermatoses.

The production of these novel light screening agents (especially of skin protection preparations for everyday cosmetics) comprises incorporating the compound of formula I preferably in combination with a UV B filter, in a cosmetic base which is usual for light screening agents.

As UV B filters in the scope of the present invention, i.e. as substances having absorption maxima between about 290 and 320 nm, there can be mentioned usual UV B filters, for example the following organic compounds which belong to the widest classes of substance:

1) p-aminobenzoic acid derivatives such as ethyl p-aminobenzoate and other esters such as propyl, butyl and isobutyl p-aminobenzoate; ethyl p-dimethylaminobenzoate, glyceryl p-aminobenzoate, amyl p-dimethylaminobenzoate; and octyl p-N,N-dimethyl-aminobenzoate, 2a) cinnamic acid derivatives such as 2-ethoxyethyl p-methoxycinnamate, 2-ethylhexyl (or pentyl) p-methoxycinnamate, p-methoxycinnamic acid ester mixtures and cinnamic acid ester mixtures, 2b) malonic acid derivatives, e.g. phenylmethylene malonic acid ester and 2a) and 2b) bonded to siloxanes, e.g. the compounds denotes as "polysiloxane A" in EP 709 080, 3) heterocyclic nitrogen compounds such as 2-phenyl-benzimidazole derivatives, e.g. 2-phenylbenzimidazole-5-sulphonic acid, 4) salicylic acid derivatives, e.g. methyl salicylate, homomenthyl salicylate, phenyl salicylate and ethylhexyl salicylate, 5) benzophenone derivatives such as 4-phenylbenzophenone, isooctyl 4-phenylbenzophenone-2-carboxylate, 2-hydroxy-4-methoxybenzophenone-5-sulphonic acid, 2,2'-dihydroxy-4-methoxybenzophenone, bis(2,4-dihydroxyphenyl)methanone and 2-hydroxy-4-octoxybenzophenone, 6) gallic acid derivatives such as digalloyl trioleate, 7) arylidenecycloalkanones such as benzylidenecamphor, p-tert.-butylbenzylidenecamphor (preferred) or methylbenzyl-idenecamphor, 8) anthranilic acid derivatives such as menthyl anthranilate, 9) hydroxyphenylbenztriazole, 10) acrylates, e.g. 2-ethylhexyl 2-cyano-3,3-diphenyl-acrylate (octocrylene) and ethyl 2-cyano-3,3-diphenylacrylate, and 11) microcrystalline powder, e.g. microcrystalline $TiO_2$, ZnO and $Fe_2O_3$.

The compounds set forth under 2) are preferred, particularly 2-ethylhexyl p-methoxycinnamate.

As cosmetic bases usual for light screening agents in the scope of the present invention there can be used any conventional preparation which corresponds to the cosmetic requirements, e.g. creams, lotions, emulsions, salves, gels, solutions, sprays, sticks and milks; see also Kosmetik, Entwicklung, Herstellung and Anwendung Kosmetischer Mittel, ed. Wilfried Umbach, Georg Thieme Vertrag Stuttgart—New York 1988, Sunscreens, Development, Evaluation and Regulatory Aspects, ed. N. Y. Lowe, N. A. Shaath, Marcel Dekker, Inc. New York, Basel, 1990.

The light screening effect also depends on the base which is used. Further, in the case of the same base the intensity of the light screening effect depends on the active substance conentration. Suitable concentrations are e.g. 1–6%, preferably 2–5%, of the compound of formula I in th e cosmetic preparation. The ratio of compound I to UV B filter is not critical. However, for economic reasons it is, for example, 1–2 parts of UV B filter to 1 part of compound I Having regard to their lipophilicity, the compounds I can be incorporated well in oil-containing and fat-containing cosmetic preparations.

With respect to the lipophilicity, the novel compounds are superior to the known substituted triazines employed as industrial light screening agents, see U.S. Pat. No. 3,896,125 and, respectively, DAS 1 241 452, in that all fulfill the criteria which are required in the present instance, namely a solubility of ≧1% in cosmetic solvents, such as e.g. Cétiol LC (cocoyl caprylate/caprate), Lexorez 100 (glycerol diethylene glycol adipate cross polymer) or Crodemol DA (diisopropyl adipate). On the other hand, solubilities of only 0.5% or below are achieved in the case of the previously known structures.

The compound of Example 1 is an especially preferred compound in this respect.

Furthermore, the structural features (and therewith the accessibility) are also simpler in the present case.

The compounds I are novel. They also form an object of the present invention.

The access to I can be illustrated as follows:

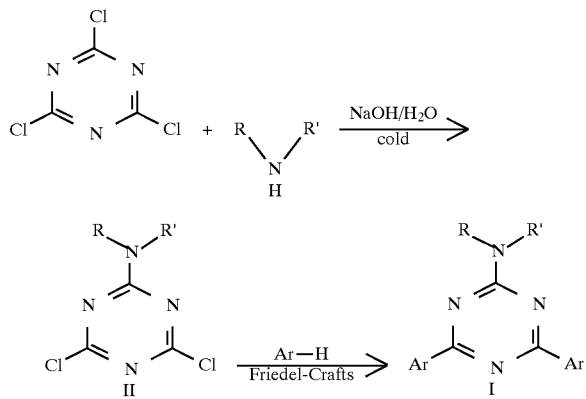

The process from II→I thus comprises reacting a compound of the formula

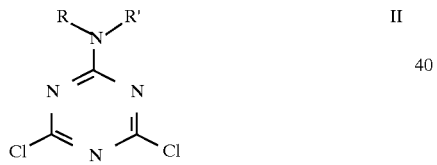

with a substance corresponding to the above radical Ar, e.g. under the conditions of the Friedel-Crafts reaction.

Free hydroxy groups in $R^2$ and/or $R^3$ can be etherified if desired.

The reaction of the reaction partners can be carried out under the conditions which are usual, which are well-known, for the Friedel-Crafts reaction. The reaction may be carried out in the presence or absence of a solvent. Suitable solvents are aprotic organic solvents, e.g. toluene, nitrotoluene, chloro-, dichloro- and trichlorobenzene, hydrocarbons (e.g. isooctane), chlorinated hydrocarbons, nitroalkanes, sulpholane (tetramethylenesulphone) carbon disulphide, sulphur dioxide, etc. as well as mixtures thereof. The known catalysts are conveniently used, i.e. Lewis acids such as aluminium chloride, tin chloride, zinc chloride, titanium tetrachloride, boron trifluoride, etc. The temperature range is conveniently that of about 10° C. to about 220° C., preferably between about 80° C. and 150° C.

One possible access to II is illustrated above, with the methodology being described in detail by J. T. Thurston et al., J. Amer. Chem. Soc. 73, 2981 (1951), and will be evident from the forgoing Scheme and the following Examples.

The etherification of free hydroxy groups can be effected in a manner known per se, e.g. by reacting a phenol of general formula I with an ether-forming reagent, e.g. an alkyl halide (or alkenyl halide or alkynyl halide), an alkyl tosylate or an epoxide. The reaction can be performed in the absence of a solvent (preferred) or in the presence of solvents (e.g. diethyl ether, ethanol, acetone, DMSO, DMF, toluene, etc) under neutral conditions or optionally using acids (e.g. $H_2SO_4$, etc.) or also, preferably, using bases (pyridine, trimethylamine, NaOH, NaOEt, tert.-butyl-ONa, NaH, LiH, K, Na, $K_2CO_3$, $Na_2CO_3$, $NaHCO_3$, butyllithium, etc.).

In addition, phase transfer reagents, e.g. tetrabutylammonium bromide, crown ethers, etc. can be employed.

As reagents there accordingly come into consideration e.g.: methyl iodide, methyl chloride, octyl bromide, allyl chloride, propargyl bromide, ethylene oxide, propylene oxide, octane-1,2-epoxide, methyl glycidyl ether, octyl glycidyl ether, etc.

A convenient temperature range is that from about 0° C. to about 150° C.

EXAMPLE 1

4,4'-{6-[Bis-(2-ethyl-hexyl)-amino]-s-triazine-2,4-diyl}-diresorcinol.

a) A preparation of 4,6-dichloro-[1,3,5]-triazin-2-yl-bis-(2-ethyl-hexyl)-amine: 18.4 g (0.1 mol) of cyanuric chloride was suspended in 75 ml of acetone and added dropwise to 90 ml of cooled water. Thereupon, 24.1 g (0.1 mol) of bis-(2-ethyl-hexyl)-amine and subsequently 4 g (0.1 mol) of NaOH, dissolved in 14 ml of water, were added dropwise. The suspension was stirred at 20° C. for two hours, then poured into 200 ml of water and extracted with ethyl acetate. The dried and concentrated, combined, organic phases gave 35 g of a clear oil of the desired dichlorotriazine, the structure of which was determined by MS (388=M+).

b) A suspension of 16.5 g (0.124 mol) of $AlCl_3$ and 23.2 g (0.06 mol) of the oil obtained above in 150 ml of toluene was heated to 70° C. and treated with 14.5 g (0.132 mol) of resorcinol in 19 g of sulpholane. This mixture was stirred at 110° C. for 24 hours and thereupon partitioned between water and ethyl acetate. The ethyl acetate phase was extracted with 2N NaOH solution and the NaOH extract was acidified with dilute HCl and filtered. The product obtained was washed neutral with NaCl solution and recrystallized from hexane/diethyl ether.

Yield 21.9 g of a fine powder of the desired product. Melting point 141°–143° C., UV 339 nm (E=648).

EXAMPLE 2

4,4'-[6-(Di-n-octyl-amino)-s-triazine-2,4-diyl]-diresorcinol.

The procedure in Example 1 was carried out, but one equivalent of di-n-octylamine was used in place of bis-(2-ethyl-hexyl)-amine.

The yield in the 1st step was 76% and in the 2nd step 51% of theoretical. M.p.: 165°–67° C. UV 338 nm (E=724).

EXAMPLE 3

4,4'-[6-(Di-n-pentyl-amino)-s-triazine-2,4-diyl]-diresorcinol.

The procedure in Example 1 was carried out, but one equivalent of di-n-pentylamine was used in place of bis-(2-ethyl-hexyl)-amine.

The yield in the 1st step was 81% and in the 2nd step 46% of theoretical. M.p.: 190°–92° C. UV 339 nm (E=681).

EXAMPLE 4

4,4'-[6-(Di-isobutyl-amino)-s-triazine-2,4-diyl]-diresorcinol.

The procedure as in Example 1 was carried out, but one equivalent of di-isobutylamine was used in place of bis-(2-ethyl-hexyl)-amine.

The yield in the 1st step was 89% and in the 2nd step 63% of theoretical. M.p.: 210°–20° C. UV 338 nm (E=736).

EXAMPLE 5

4,4'-[6-(Allyl-2-ethyl-hexyl-amino)-s-triazine-2,4-diyl]-diresorcinol.

The procedure as in Example 1 was carried out, but one equivalent of allyl-2-ethyl-hexylamine was used in place of bis-(2-ethyl-hexyl)-amine. The yield in the first step was 94% and in the 2nd step 20% of theoretical. M.p.: 90°–94° C. UV 340 nm (E=896).

The allyl-2-ethyl-hexylamine was prepared as follows: 17.8 ml of 2-ethyl-hexyl bromide were added dropwise at 0° C. to 60 ml of allylamine. The mixture was heated slowly to reflux, refluxed for 18 hours and the excess allylamine was subsequently distilled off. The residue was taken up in ether and washed with aqueous NaOH and aqueous NaCl, and again concentrated. There were obtained 11.9 g (63%) of a yellowish oil of allyl-2-ethyl-hexylamine, the identity of which was confirmed by NMR, IR and MS.

EXAMPLE 6

4,4'-{6-[Bis(2-ethyl-hexyl)-amino]-2,4-bis[4-(3-butoxy-2-hydroxy-propoxy)-2-hydroxy-phenyl]-[1,3,5]-triazine 2.15 g of 4,4'-{6-[bis-(2-ethyl-hexyl)-amino]-s-triazine-2,4-diyl}-diresorcinol (prepared according to Example 1) and 22 mg of tetrabutylammonium chloride were heated to 130° C. in 40 ml of butyl glycidyl ether for 24 hours. Thereafter, the cooled, yellow solution was washed with water and concentrated in a water-jet vacuum and subsequently in a high vacuum at 0.05 Torr and chromatographed over silica gel with hexane/ethyl acetate. There were obtained 2.35 g of a yellowish oil, the identity of which was confirmed by NMR, IR and MS (796=M+). UV 319 nm (E=346).

EXAMPLE 7

4,4'-{6-[Bis(2-ethyl-hexyl)-amino]-2.4-bis(4-methyl-2-hydroxy-phenyl)-[1,3,5]triazine.

10 g of the dichloro-triazine described in Example 1 was heated to 120° C. for 4 days together with 6.1 g of m-cresol and 6.9 g of AlCl$_3$ in 100 ml of xylene. The reaction mixture was partitioned between water and ethyl acetate, the organic phase was concentrated and chromatographed through silica gel with hexane/toluene. Yield 1.9 g of the above, crystalline product, m.p. 75°–76° C, MS (532=M+), UV 340 nm (E=373).

EXAMPLE 8

4,4'-{6-Bis(2-ethyl-hexyl)-amino)-s-triazine-2,4-diyl}-di-naphthoresorcinol.

The procedure as in Example 1 was carried out, but in b) 1,3-naphthoresorcinol was used in place of resorcinol and the reaction mixture was heated to 130° C. for 18 hours. After working-up, the crude product was chromatographed over silica gel in ethyl acetate/hexane =1:1.

The desired product was obtained: m.p. 100°–105° C. UV 382 nm (E=384).

EXAMPLE 9

4,4'-{6-(Dibutyl-amino)-2,4-bis(2,4-dihydroxy-5-hexyl-phenyl)-[1,3,5]-triazine.

The procedure as in Example 1 was carried out, but in a) di-n-butylamine was used in place of bis-(2-ethyl-hexyl)-amine and in b) 4-hexylresorcinol was used in place of resorcinol. The mixture was heated to 110° C. for 2 days. After working-up, the crude product was crystallized from toluene/ethanol.

The desired product was obtained: m.p. 203°–206° C. UV 350 nm (E=350).

EXAMPLE 10

4,4'-{6-(Bis-(2-ethyl-hexyl)-amino)-2,4-bis(2,4-dihydroxy-3-methyl-phenyl)-[1,3,5]-triazine.

The procedure as in Example 1 was carried out, but in b) 1,6-dihydroxytoluene was used in place of resorcinol and the reaction mixture was heated to 130° C. for 2 hours. After working-up, the crude product was recrystallized twice in acetonitrile.

The desired product was obtained: m.p. 90°–93° C. UV 340 nm (E=653).

EXAMPLE 11

4,4'-{6-(N-Isopentyl-N-3,5,5-trimethyl-hexyl-amino)-s-triazine-2,4-diyl}-diresorcinol.

The procedure as in Example 1 was carried out, but in a) N-isopentyl-N-3,5,5-trimethyl-hexyl-amine was used in place of bis-(2-ethyl-hexyl)-amine.

The product named above was obtained in 52% yield: m.p. 187°–189° C. UV 337.5 nm (E=665).

N-Isopentyl-N-3,5,5-trimethyl-hexyl-amine was accessible from "isononylamine" (Hoechst) and isovaleroyl chloride in aqueous KOH at 0°–20° C. and subsequent reduction with LiAlH$_4$ in ether under reflux temperature.

EXAMPLE 12

| Sunscreen emulsion (o/w) | Parts by weight |
|---|---|
| A | |
| Parsol MCX (octyl methoxycinnamate) | 5.0 |
| triazine of Example 1 | 3.0 |
| cetyl alcohol | 1.00 |
| diethylene glycol monostearate | 0.25 |
| Cetiol LC (cocoyl capryl/caprate) | 7.00 |
| MPOB/PPOB 70/30 (methyl + propylparaben ester of 4-hydroxybenzoic acid) | 0.25 |
| EDTA—Na$_2$ and | 0.1 |
| Amphisol K (potassium cetyl phosphate) | 1.00 |
| were combined in a reactor, melted and thereupon treated at 90° C. with a mixture of | |
| B | |
| Pemulen TR-1 1% (C10–C30 alkyl acrylate cross polymer) | 20.0 |
| water | 56.4 |
| propylene glycol | 5.00; |
| finally | |
| KOH 10% | 0.80 |
| and | |
| C | |
| an odorant composition | 0.20 |
| were admixed at 40° C. | |

EXAMPLE 13

| Silicon-water emulsion (lotion) | Parts by weight |
|---|---|
| A | |
| Gilugel SIL5 (cyclomethicone and aluminium/ magnesium hydroxide stearate) | 5.0 |
| was melted in a reactor and treated with a mixture of | |
| B | |
| Silicone 3225 C (silicone oil) | 10.0 |
| Silicone 245 (cyclomethicone) | 5.0 |
| Witconol PPM (PPG-3 myristyl ether) | 2.0 |
| and Parsol MCX | 5.0 |
| and subsequently with a mixture of | |
| C | |
| triazine of Example 1 | 2.0 |
| Finsolv TN (C12–15-alkyl benzoate) | 5.0 |
| Phenonip (phenoxyethanol & methylparaben & ethylparaben & propylparaben & butylparaben) | 0.6 and |
| BHT (butylhydroxytoluene) | 0.05 |
| EDTA—Na$_2$ | 0.1 |
| and with | |
| water | 58.85 |
| and dissolved therein | |
| NaCl | 0.5. |
| This mixture was heated to 85° C. in a water bath and treated with | |
| E | |
| TiO2 | 1.9 |
| and a mixture of | |
| Hyasol (soduim hyaluronate) | 2.0 |
| and vitamin E acetate (tocopheryl acetate) | 2.0 |

EXAMPLE 14

| Sunscreen lotion (w/o) | Parts by weight |
|---|---|
| A | |
| Parsol MCX | 5.0 |
| triazine of Example 1 | 3.0 |
| Arlacel 481 (glycerol/sorbitan fatty acid ester) | 9.0 |
| Elfacos C26 (hydroxyoctacosanyl hydroxystearate) | 5.0 |
| petroleum special (petrolatum) | 2.0 |
| Vaseline oil | 10.0 |
| Cetiol LC | 10.0 |
| EDTA—Na$_2$ | 0.1 |
| and | |
| Phenonip | 0.6 |
| were mixed in a reactor and melted; a mixture of | |
| B | |
| water | 21.5 |
| sorbtol 70% | 5.0 |
| in glycerol | 3.0 |
| and a mixture of | |
| C | |
| Parsol HS (phenylbenzimidazolesulphonic acid) | 2.00 |
| KOH 10% | 4.29 |
| in water | 19.31 |
| were added at 90° C. in succession to the original mixture. Finally | |
| Sunmild 718 (an odorant composition) | 0.2 |
| was admixed at 40° C. | |

I claim:

1. The compound of 4,4'-{6-[Bis(2-Ethyl-hexyl)-amino]-s-triazine-2,4-diyl}-diresorcinol.
2. The compound of 4,4'-[6-(Di-isobutyl-amino)-s-triazine-2,4-diyl]-diresorcinol.
3. The compound of 4,4'-[6-(Di-n-octyl-amino)-s-triazine-2,4-diyl]-diresorcinol.
4. The compound of 4,4'-[6-(Allyl-2-ethyl-hexyl-amino)-s-triazine-2,4-diyl]-di-resorcinol.
5. The compound of 4,4'-[6-(Di-n-pentyl-amino)-s-triazine-2,4-diyl]-diresorcinol.
6. The compound of 4,4'-{6-(N-Isopentyl-N-3,5,5-trimethyl-hexyl-amino)-s-triazin-2,4-diyl}-diresorcinol.

* * * * *